(12) United States Patent
Yamamoto

(10) Patent No.: US 7,875,570 B2
(45) Date of Patent: Jan. 25, 2011

(54) PROCESS FOR PRODUCING TITANIUM-CONTAINING SILICON OXIDE CATALYST, THE CATALYST, AND PROCESS FOR PRODUCING OLEFIN COMPOUND WITH THE CATALYST

(75) Inventor: Jun Yamamoto, Sodegaura (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 581 days.

(21) Appl. No.: 11/720,649

(22) PCT Filed: Nov. 30, 2005

(86) PCT No.: PCT/JP2005/022417

§ 371 (c)(1),
(2), (4) Date: Jun. 1, 2007

(87) PCT Pub. No.: WO2006/062111

PCT Pub. Date: Jun. 15, 2006

(65) Prior Publication Data

US 2009/0234143 A1    Sep. 17, 2009

(30) Foreign Application Priority Data

Dec. 6, 2004  (JP)  .............................. 2004-352357
Dec. 6, 2004  (JP)  .............................. 2004-352358

(51) Int. Cl.
*B01J 21/08* (2006.01)
(52) U.S. Cl. .................. 502/242; 549/529; 549/531
(58) Field of Classification Search ................. 502/242; 549/523, 529, 531
See application file for complete search history.

(56) References Cited

U.S. PATENT DOCUMENTS

| 6,284,696 B1 | 9/2001 | Koya et al. |
| 2004/0067846 A1 | 4/2004 | Yamamoto et al. |
| 2006/0155137 A1 | 7/2006 | Yamamoto |

FOREIGN PATENT DOCUMENTS

| JP | 10-072212 A | 3/1998 |
| JP | 11-309378 A | 11/1999 |
| JP | 2002-224563 A | 8/2002 |
| JP | 2004-195379 A | 7/2004 |

OTHER PUBLICATIONS

A. Corma et al., "One step synthesis of highly active and selective epoxidation catalysts formed by organic-inorganic Ti containing mesoporous composites", Chem. Commun., (1998), pp. 1899-1900.
K. Yamamoto et al., "Synthesis and Catalysis of Ti-MCM-41 Materials with Organic-Inorganic Hybrid Network", Chemistry Letter, (2001), pp. 648-649.
Y. Yang et al., "Synthesis and catalytic properties of organically modified Ti-HMS", Studies in Surface Science and Catalysis 141, (2002), pp. 189-196.
M.P. Kapoor et al., "Titanium containing inorganic-organic hybrid mesoporous materials with exceptional activity in epoxidation of alkenes using hydrogen peroxide", J. Mater. Chem., (2002), 12, pp. 3078-3083.

*Primary Examiner*—Janet L Andres
*Assistant Examiner*—David E Gallis
(74) *Attorney, Agent, or Firm*—Sughrue Mion, PLLC

(57) ABSTRACT

A process for producing a titanium-containing silicon oxide catalyst, which comprises the following steps A and B; a catalyst obtainable by the process; and a process for producing an olefin oxide using the catalyst. Step(A) in which a silica source part or all of which is a silicon compound having a silicon atom having a hydrocarbon group directly bonded thereto is mixed by stirring with a titanium source and a template solution to obtain a solid containing the catalyst component and template, the rate of water in the solvent in the template solution being 50% by weight or lower or a step in which a silica source which comprises a combination of an organic silica source comprising a silicon compound having a silicon atom having a hydrocarbon group directly bonded thereto with a silicon compound having no carbon-silicon bond is mixed by stirring with a titanium source and the template solution to obtain a solid containing the catalyst component and the template, the addition of the silica source to the template solution being conducted so as to satisfy the relationship: (amount of the organic silica source added in the first half)>(amount of the organic silica source added in the latter half). Step B: a step in which the template is removed from the solid obtained in the step A.

8 Claims, No Drawings

PROCESS FOR PRODUCING TITANIUM-CONTAINING SILICON OXIDE CATALYST, THE CATALYST, AND PROCESS FOR PRODUCING OLEFIN COMPOUND WITH THE CATALYST

TECHNICAL FIELD

The present invention relates to a process for producing a titanium-containing silicon oxide catalyst, said catalyst, and a process for producing an olefin oxide compound with the catalyst.

BACKGROUND ART

Methods of obtaining an olefin oxide compound from an olefin type compound and a hydroperoxide in the presence of a catalyst, are publicly known. As a catalyst used herein, a titanium-containing silicate is listed, and attempts for improvement of a hydrophobicity to obtain a high performance catalyst, are tried. For example, JP 10-072212 A, JP 2002-320860 A, Chem. Commun., (1998) 1899, Chem. Lett., (2001) 648, Stud. Surf. Sci. catal., 141 (2002) 189 and J. Mater. Chem., 12 (2002) 3078 disclose specified titanium-containing silicon oxide catalysts in which the hydrophobicity was improved by using a silicon compound in which a hydrocarbon group is directly bonded to a silicon atom. However, it was difficult to say that these catalysts were sufficiently satisfied from the viewpoint of realization of higher activity and selectivity.

DISCLOSURE OF THE INVENTION

An object of the present invention is to provide a process for producing a titanium-containing silicon oxide catalyst which can be used for obtaining an olefin oxide compound from, for example, a hydroperoxide and an olefin type compound and can exhibit high activity and selectivity, and a catalyst obtainable by the process.

Namely, the present invention relates to a process for producing a titanium-containing silicon oxide catalyst satisfying all of the following conditions (1) to (3), which comprises the following A and B steps:

(1) an average pore diameter of 10 Å or more,
(2) a pore diameter of 90% or more of the total pore volume of 5 to 200 Å, and
(3) a specific pore volume of 0.2 cm$^3$/g or more: and Step A:

(I) a step of obtaining a solid containing a catalyst component and a template by using a silicon compound in which a part or all of a hydrocarbon group is directly bonded to a silicon atom, as a silica source, and mixing the silica source with a titanium source and a solution of the template by stirring, wherein the rate of water in a solvent in the solution is 50% by weight or lower, or (II) a step of obtaining a solid containing a catalyst component and a template by using an organic silica source composed of a silicon compound in which a hydrocarbon group is directly bonded to a silicon atom and an inorganic silica source composed of a silicon compound not having a carbon-silicon bonding, as a silica source, and mixing the silica source with a titanium source and a solution of the template by stirring, wherein the following expression is satisfied in the addition of the silica source to the solution of the template, Amount of the organic silica source added in the first half>Amount of the organic silica source added in the latter half (wherein, the first half means a period taken from the initiation of the addition to completion of the addition of the half mole of the whole amount (mole) of the all silica source); and Step B: a step of removing the template from the solid obtained in the step A.

Further, the present invention provides a titanium-containing silicon oxide catalyst obtainable by the above-described process.

Still further, the present invention provides a process for producing an olefin oxide compound, which comprises reacting an olefin type compound with a hydroperoxide in the presence of the titanium-containing silicon oxide catalyst obtainable by the above-described process.

BEST MODE FOR CARRYING OUT THE INVENTION

The catalyst obtainable by the present invention is a catalyst composed of a titanium-containing silicon oxide catalyst satisfying the following conditions (1) to (3).

The condition (1) is that an average pore diameter of the catalyst is 10 Å or more.

The condition (2) is that a pore diameter of 90% or more of the total pore volume of the catalyst is 5 to 200 Å.

The condition (3) is that a specific pore volume of the catalyst is 0.2 cm$^3$/g or more. Herein, the specific pore volume means a pore volume per 1 g of the catalyst.

Measurements of these conditions (1) to (3) can be conducted by conventional methods such as a physical adsorption method using a gas such as nitrogen, argon or the like.

The catalyst obtained in the present invention may or may not have a peak showing an interplanar spacing (d) in an X-ray diffraction (XRD). The peak showing an interplanar spacing (d) as herein referred to means a peak due to the crystallinity and regularity of a solid, and a broad peak due to an amorphous part may exist.

The catalyst preferably has an absorption peak in the region of 960±5 cm$^{-1}$ in the infrared absorption spectrum from the viewpoint of high activity. This peak is assumed to correspond to that of titanium introduced into the silica skeleton.

The catalyst satisfying the above-described conditions (1) to (3) is produced by a process containing the steps A and B described below.

As the step A, there are adopted:

(I) a step of obtaining a solid containing a catalyst component and a template by using a silicon compound in which a part or all of a hydrocarbon group is directly bonded to a silicon atom, as a silica source, and mixing the silica source with a titanium source and a solution of the template by stirring, wherein a content of water in a solvent of the solution is 50% by weight or lower; or (II) a step of obtaining a solid containing a catalyst component and a template by using an inorganic silicon compound not having a hydrocarbon group which is directly bonded to a silicon atom and a carbon-silicon atom bonding, as a silica source, and mixing the silica source with a titanium source and a solution of the template by stirring, wherein the following expression is satisfied in the addition of the solution of the template to the silica source.

Amount of the organic silicon compound added in the first half>Amount of the organic silicon compound added in the latter half (wherein the first half means a period taken from the initiation of the addition to completion of the addition of the half mole of the amount (mole) of the total silica source).

In the (I) of the step A, when the silica source, the titanium source and the template are mixed and stirred, a solvent in which a rate of water is 50% by weight or lower is used as a solvent for the template.

When the above-described material used is solid-like, it is good to use after dissolving or dispersing it in the solvent.

The mixing method is not particularly restricted, but it is generally preferable to add the silica source and the titanium source in the template solution.

Further, in the (II) of the step A, it is essential to satisfy the following relational expression in addition of the silica source to the template solution.

Amount of the organic silica source added in the first half period>Amount of the organic silica source added in the latter half period (the first half period means a period taken from the initiation of the addition to completion of the addition of the half mole of the whole amount (mole) of the silica source).

Particularly, it is preferable to add whole amount of the organic silica source to the template solution in the first half period.

If the above-described conditions are satisfied, the organic silica source and the inorganic silica source may be added after mixing them to adjust to desired concentrations, may be respectively added step-wise without mixing, or may be added by a combination of these methods, and the method is not especially limited.

In the (II) of the step A, there are characteristics that reduction of the amount of the organic silica source required for obtain a catalyst of high activity and high selectivity becomes possible and a high performance catalyst can be obtained at low cost.

Examples of the silicon compound, in which a hydrocarbon group is directly bonded to a silicon atom, used in the present invention as a raw material, include monoalkyltrialkoxysilanes, dialkyldialkoxysilanes, trialkylmonoalkoxysilanes, bis(trialkoxysilyl)alkane, monoaryltrialkoxysilane, diaryldialkoxysilane, and bis(trialkoxysilyl)arene. These may be used alone or may be used as a mixture of two or more kinds. Among them, monoalkyltrialkoxysilanes and/or monoaryltrialkoxysilanes are preferably used, and examples of the alkyl group or aryl group include hydrocarbon groups having 1 to 16 carbon atoms such as methyl, ethyl, propyl, butyl, vinyl, propenyl, cyclopentenyl, cyclohexenyl, phenyl, tolyl, xylyl and naphtyl. Further, the above-described alkyl group and aryl group may have a substituent group containing N, O, P, halogen or the like. As the alkoxy group, alkoxy groups having 1 to 6 carbon atoms such as methoxy, ethoxy, propoxy and butoxy, are listed. Specific examples of the organic silica source can include trimethoxymethylsilane, trimethoxyphenylsilane, dimethoxydimethylsilane, triethoxymethylsilane, triethoxyphenylsilane, diethoxydiethylsilane, tripropoxymethylsilane and tributoxymethylsilane.

For strengthening a silica skeleton in the catalyst, amorphous silica or a silicon compound not having carbon-silicon bonding (inorganic silica source) such as an alkoxysilane (e.g. tetramethylorthosilicate, tetraethylorthosilicate, tetrapropylorthosilicate) may be used together with the above-described organic silica source, and it is preferably used as a mixture with the organic silica source.

In the step A (I), when the mixture of the organic silica source and inorganic silica source is used, the mixing rate is not particularly restricted, but the organic silica source of preferably 5% by mole or more, more preferably 5 to 50% by mole, further preferably 10 to 30% by mole (the total of the organic silica source and the inorganic silica source is 100% by mole) is mixed.

In addition, the rate is also not particularly restricted in the step A (II), but the used amount of the organic silica source is preferably within the range of 5 to 50% by mole, more preferably 10 to 30% by mole (the total of the organic silica source and the inorganic silica source is 100% by mole).

The titanium source includes titanium alkoxides such as tetramethyl titanate, tetraethyl titanate, tetrapropyl titanate, tetraisopropyl titanate, tetrabutyl titanate, tetraisobutyl titanate, tetra-2-ethylhexyl titanate, tetraoctadecyl titanate; and titanium (IV) oxyacetylacetonate and titanium (IV) diisopropoxybisacetylacetonate; and titanium halides (e.g. titanium tetrachloride, titanium tetrabromide and titanium tetraiodide); titanyl sulfate and the like. As the template, anyone of cationic surfactants such as alkylammoniums, dialkylammoniums, trialkylammoniums, benzylammonium and alkylpyridiniums; anionic surfactants such as alkyl sulfate ions and alkylphosphate ions, nonion surfactants such as polyalkylene oxides, block copolymer thereof and alkylamines can be applied. Among them, quaternary ammonium ions represented by the general formula (I) or alkylpiridinium ions are preferably used.

$$[NR^1R^2R^3R^4]^+ \qquad (I)$$

(wherein, $R^1$ represents a linear or branched hydrocarbon group having 2 to 36 carbon atoms, and $R^2$ to $R^4$ represent an alkyl group having 1 to 6 carbon atoms).

$R^1$ is a linear or branched hydrocarbon group having 2 to 36 carbon atoms, preferably 10 to 18 carbon atoms.

$R^2$ to $R^4$ are an alkyl group having 1 to 6 carbon atoms, and preferably each of $R^2$ to $R^4$ is a methyl group.

Specific examples of the quaternary ammonium ion represented by the general formula (I) include hexadecyltrimethylammonium, dodecyltrimethylammonium, benzyltrimethylammonium and dimethyldidodecylammonium, and the alkylpyridinium ion includes a cation such as hexadecylpiridinium. In addition, the compounds for the template may be used alone or as a mixture of several kinds.

Examples of the solvent for dissolving the template include water and alcohols such as methanol, ethanol, n-propanol, 2-propanol, n-butanol, sec-butanol, t-butanol, vinyl alcohol, allyl alcohol, cyclohexanol and benzyl alcohol, and diols, mixtures thereof and the like.

In the above-described step A (I), the rate of water contained in the solvent dissolving the template, is essentially 50% by weight or lower, preferably 5 to 40% by weight, and more preferably 10 to 30% by weight. By using the solvent, a catalyst realizing high activity and high selectivity, can be obtained.

Next, the step A (II) is described.

As a silica source, a silicon compound having a hydrocarbon group which is directly bonded to a silicon atom (organic silica source) and an inorganic silica source not having a carbon-silicon atom bonding, are used, and the silica source, the titanium source and the template are mixed and stirred in the solvent thereby to obtain a solid containing a catalyst component and the template, wherein the following relational expression is satisfied in the addition of the silica source to the solution of the template:

Amount of the organic silicon compound added in the first half period>Amount of the organic silicon compound added in the latter half period (wherein the first half means a period taken from the initiation of the addition to completion of the addition of the half mole of the amount (mole) of the tatal silica source).

It is possible to produce a titanium-containing catalyst of high activity and high selectivity by applying the adding method of the silica source to the template solution described above.

As the organic silica source and inorganic silica source used in the method of the step A (II), compounds described above are used, and as the compound of the titanium source and the template, compounds described before can be also used. Further, in the step A (II), though solvents above-exemplified can be used as a solvent of the template, the content of water is not restricted and further, water may not be contained. However, the solvent for the template used in the step A (II) is preferably a solvent satisfying the conditions in the step A(I).

The present invention is described in more detail, but it can be applied to both of the steps A (I) and A(II) unless otherwise noted.

The amount used of the titanium source based on the silica source is preferably from $10^{-5}$ to 1, more preferably from 0.00008 to 0.4 in terms of molar ratio. The amount used of the quaternary ammonium ion based on the total amounts of the silica source and titanium source is preferably from $10^{-2}$ to 2 in terms of molar ratio.

Further, for promoting the reaction of the silica source with the titanium source, it is preferable to impart alkalinity or acidity to the mixed solution. As the alkali source, quaternary ammonium hydroxides are preferable, and examples thereof include tetramethylammonium hydroxide, tetraethylammonium hydroxide and tetrapropylammonium hydroxide, and particularly, when a hydroxide of the quaternary ammonium ion represented by the general formula (I) is used as the template, the addition of the alkali source is not necessarily required, therefore, use thereof is preferable. Further, examples of the acid include inorganic acids such as hydrochloric acid, sulfuric acid and nitric acid, and organic acids such as formic acid, acetic acid and propionic acid.

The mixing and stirring temperature is usually from −30 to 100° C. A solid is formed by mixing and stirring, and the solid may be aged for further growth thereof. The aging time is usually 180 hours or less, and the aging temperature is usually from 0 to 200° C. When heating is required in aging, it is preferable that the mixture is transferred into a pressure vessel and heating is conducted in a closed pressure vessel for avoiding vaporization of the solvent.

The step B is a step for removing the template from the solid.

The removal of the template can be accomplished by subjecting the solid containing the catalyst component and the template to solvent extraction or calcination, and the solvent extraction is preferable. A technique for extracting a template with a solvent is reported by Whitehurst et al. (see U.S. Pat. No. 5,143,879)

The solvent used in extraction may include a solvent which can dissolve a compound used as the template, and oxa- and/or oxo-substituted hydrocarbons having carbon atoms of 1 to about 12 in a liquid state at room temperature can be generally used. Suitable examples of such solvents include alcohols, ketones, ethers (acyclic and cyclic) and esters. Examples thereof include hydroxy-substituted hydrocarbons such as methanol, ethanol, ethylene glycol, propylene glycol, isopropanol, n-butanol or octanol; oxo-substituted hydrocarbons such as acetone, diethyl ketone, methyl ethyl ketone or methyl isobutyl ketone; ethers of a hydrocarbon such as diisobutyl ether and tetrahydrofuran; esters of a hydrocarbon such as methyl acetate, ethyl acetate, butyl acetate or butyl propionate, and the like, but, from the viewpoint of solubility to the template, alcohols are preferable, and among them, methanol is further preferable. The weight ratio of the extracting solvent to the solid containing the catalyst component and the template should not be limited, but is usually from 1 to 1000, preferably from 5 to 300.

For improving efficiency of the extraction, an acid or a salt thereof may be added to these solvents.

Examples of acids used include inorganic acids such as hydrochloric acid, sulfuric acid, nitric acid and bromic acid, organic acids such as formic acid, acetic acid and propionic acid. Examples of salts thereof include alkali metal salts, alkaline earth metal salts and ammonium salts.

The concentration in the solvent of the acid or salt thereof to be added is preferably 10 mol/l or less, further preferably 5 mol/l or less. When the concentration in the solvent of the acid or salt to be added is too high, the catalytic activity may be lowered by elution of titanium in the catalyst.

After adequately mixing the extraction solvent with the solid containing the catalyst component and the template, a liquid phase portion is separated by a method of filtration, decantation or the like. This operation is repeated required times. Further, it is also possible to extract the template by a method of filling the solid containing the catalyst component and the template in a tube or the like and passing a extraction solvent through there. Completion of the extraction can be known by, for example, analyzing the liquid portion. The extraction temperature is preferably 0 to 200° C., further preferably 20 to 100° C. When the boiling point of the extraction solvent is low, the extraction may be carried out under pressure.

The template in the solution obtained by the extraction treatment is recovered and can be also recycled as a template material in the step A.

In addition, like wise the template, the solvent used for extraction can be purified through a usual distillation operation or the like and also recycled.

The extracting solvent contained in the solid after the extracting operation can be removed by drying operation, and further, when silylation is conducted subsequent thereto, the solvent can be removed by substitution with a solvent which is substantially inert to a silylating agent used in the silylation step.

In the case of removal by drying, as a drying apparatus, a conical dryer equipped with a hot-air device or vacuum device, and a plate dryer are listed.

In the case of the substitution removal, the extracting solvent contained in the solid is substituted with a solvent substantially inert to the silylating agent used in the successive silylation step. The substitution solvent used in the substitution step may be a solvent satisfying conditions of which it is substantially inert to the silylating agent and it can dissolve the extracting solvent used in the step B.

The solvent suitably used in the substitution operation, generally includes hydrocarbons, halogenated hydrocarbons, ketones, ethers, esters, N,N-substituted amides, nitriles and tertiary amines having 1 to about 12 carbon atoms and showing a liquid state at ordinary temperature, for example, hexane, cyclohexane, chloroform, benzene, toluene, xylene, acetone, diethylketone, methylethylketone, methylisobutylketone, diethylether, diisobutylether, tetrahydrofuran, dioxane, methylacetate, ethylacetate, dimethylformamide, acetonitrile, pyridine, triethylamine and dimethysufoxide. A preferable solvent for substitution is hydrocarbons in connection with the subsequent silylation step, and among them, toluene is the most preferable. These solvents can be used respectively alone or as a mixture solution of several kinds.

In the substitution operation, after the substitution solvent and the solid containing the extracting solvent obtained in the step B have been thoroughly mixed, a liquid phase part formed is separated by a method of filtration, decantation or the like. This operation is repeated required number of times. Further, it is also possible to substitute with the extracting solvent by a method of filling a reaction tube or the like with the solid containing the extracting solvent and then passing the substitution solvent through the solid.

The steps from the step B to the silylation step described after are preferably conducted with the same reactor from the viewpoint of productivity of the catalyst. Completion of the substitution operation can be known by, for example, analysis of the liquid phase part. The substitution temperature is preferably 0 to 200° C., more preferably 20 to 100° C. When the boiling point of the solvent used in the operation is low, the operation may be conducted under pressure. Further, the solvent for substitution used in the substitution step can be recycled after removing the extracting agent by a conventional method such as distillation, extraction or the like.

A solid obtained via the steps A and B in the present invention has a highly hydrophobic property, and can act as a highly active and highly selective catalyst, and furthermore, a silylated catalyst of which the performance is more improved by silylation, can be obtained.

The silylation may be carried out by a gas phase method in which the solid obtained in the step B is reacted with gaseous silylating agent, or a liquid phase method in which a silylating agent is reacted with the solid in a solvent, but, in the present invention, the liquid phase method is more preferable. Usually, when the silylation is carried out by the liquid phase method, hydrocarbons are preferably used. When the extracting solvent is removed by substitution operation, a solvent used in silylation and a solvent for substitution are not necessarily the same each other, but are preferably the same from the viewpoint of recycle the solvents.

Examples of the silylation agent include organic silanes, organic silylamines, organic silylamides and derivatives thereof, and organic silazanes and other silylation agents.

Examples of the organic silane include chlorotrimethylsilane, dichlorodimethylsilane, chlorobromodimethylsilane, nitrotrimethylsilane, chlorotriethylsilane, iododimethylbutylsilane, chlorodimethylphenylsilane, chlorodimethylsilane, dimethyl-n-propylchlorosilane, dimethylisopropylchlorosilane, t-butyldimethylchlorosilane, tripropylchlorosilane, dimethyloctylchlorosilane, tributylchlorosilane, trihexylchlorosilane, dimethylethylchlorosilane, dimethyloctadecylchlorosilane, n-butyldimethylchlorosilane, bromomethyldimethylchlorosilane, chloromethyldimethylchlorosilane, 3-chloropropyldimethylchlorosilane, dimethoxymethylchlorosilane, methylphenylchlorosilane, triethoxychlorosilane, dimethylphenylchlorosilane, methylphenylvinylchlorosilane, benzyldimethylchlorosilane, diphenylchlorosilane, diphenylmethylchlorosilane, diphenylvinylchlorosilane, tribenzylchlorosilane and 3-cyanopropyldimethylchlorosilane.

Examples of the organic silylamine include N-trimethylsilylimidazole, N-t-butyldimethylsilylimidazole, N-dimethylethylsilylimidazole, N-dimethyl-n-propylsilylimidazole, N-dimethylisopropylsilylimidazole, N-trimethylsilylamine, N-trimethylsilyldimethylamine, N-trimethylsilyldiethylamine, N-trimethylsilylpyrrole, N-trimethylsilylpyrrolidine, N-trimethylsilylpiperidine, 1-cyanoethyl(diethylamino)dimethylsilane and pentafluorophenyldimethylsilylamine.

Examples of the organic silylamide and derivatives thereof include N,O-bistrimethylsilylacetamide, N,O-bistrimethylsilyltrifluoroacetamide, N-trimethylsilylacetamide, N-methyl-N-trimethylsilylacetamide, N-methyl-N-trimethylsilyltrifluoroacetamide, N-methyl-N-trimethylsilylheptafluorobutylamide, N-(t-butyldimethylsilyl)-N-trifluoroacetamide and N,O-bis(diethylhydrosilyl)trifluoroacetamide.

Examples of the organic silazane include hexamethyldisilazane, heptamethyldisilazane, 1,1,3,3-tetramethyldisilazane, 1,3-bis(chloromethyl)tetramethyldisilazane, 1,3-divinyl-1,1,3,3-teteramethyldisilazane and 1,3-diphenyltetramethyldisilazane.

Examples of the other silylation agent include N-methoxy-N,O-bistrimethylsilyltrifluoroacetamide, N-methoxy-N,O-bistrimethylsilylcarbamate, N,O-bistrimethylsilyl sulfamate, trimethylsilyltrifluoromethane sulfonate and N,N'-bistrimethylsilylurea. The preferable silylation agent is hexamethyldisilazane.

The catalyst of the present invention is usually processed into a molded catalyst via a step for molding a solid containing the catalyst component. Though the molding step may be conducted in any stage, namely, before or after the above-mentioned template-removing step, after the solvent substitution step, and after the silylation step, it is preferable to conduct before the template-removing step from the viewpoint of suppression of degradation of catalyst properties such as specific surface area and pore volume. As the molding method, any method such as compression molding or extrusion molding may be used. An organic or inorganic binder usually used can be used in the extrusion molding, but lowering of catalyst activity may be caused by addition of the binder. In the production of the molded catalyst, the compression molding is the most preferable from the viewpoint of strength and physical properties of the catalyst.

As the compression molding, a roll press molding (briquetting, compacting), oil hydraulic press molding, tabletting and the like can be listed. The pressure in compression is usually 0.1 to 10 ton/cm$^2$, preferably 0.2 to 5 ton/cm$^2$, and further preferably 0.5 to 2 ton/cm$^2$. When the pressure is too low, the strength of a molded body is sometimes inadequate. On the other hand, when the pressure is too high, the physical properties of the catalyst sometimes become inadequate because pores are broken. In carrying out the compression molding, it is preferable that a solid containing a catalyst component contains water in a proper amount, and this can produce a molded body having a sufficient strength under a lower compressing pressure. The water content of the material to be subjected to the compression molding is preferably 1 to 70% by weight, further preferably 5 to 40% by weight. The water amount may be adjusted by a dryness degree during drying of a wet solid, and may be adjusted by adding water to an adequately dried solid.

In addition, a binder usually used or the like may be added within a range of no obstacle to a desired performance.

The shape of the molded body may be any shape such as tablet, sphere or ring. Further, the molded body may be used as it is or after pulverizing to a proper size.

The catalyst can be used for selective oxidation, for example, in addition to epoxidation of an olefin, various oxidation reactions of organic compounds because the catalyst has a high specific surface area and highly dispersed titanium active sites. Further, if desired, it is also possible to intensify acid sites of the catalyst with addition of a third component such as alumina, etc., and the catalyst can be used for alkylation, catalytic reforming, etc.

The catalyst of the present invention can be optimally can be used for production of an olefin oxide compound in which an olefin type compound is reacted with a hydroperoxide, in particular.

The olefin type compound may be acyclic, mono-cyclic, di-cyclic or poly-cyclic compounds, and mono-olefin type, di-olefin type or poly-olefin type compounds. When the number of olefin bonds is two or more, these may be a conjugated bond or non-conjugated bond. Olefin type compounds having 2 to 60 carbon atoms are usually preferred. These may have a substituent, and the substituent is preferably a relatively stable group. Examples of such the hydrocarbon include ethylene, propylene, 1-butene, isobutylene, 1-hexene, 2-hexene, 3-hexene, 1-octane, 1-decene, styrene and cyclohexene.

Apt examples of the di-olefin type compound include butadiene and isoprene. A substituent may exist, and as the example thereof, a halogen atom is listed, further various substituents containing an oxygen, sulfur or nitrogen atom together with a hydrogen and/or carbon atom, may exist. A particularly preferable olefin type compound is an olefin type unsaturated alcohol and an olefin type unsaturated hydrocarbon substituted with a halogen, and as examples thereof, allyl alcohol, crotyl alcohol, allyl chloride are listed. Particularly preferable compound is an alkene having 3 to 40 carbon atoms, and this compound may be substituted with a hydroxy group or a halogen atom.

As examples of a hydroperoxide, organic hydroperoxides can be listed.

The organic hydroperoxide is a compound represented by the general formula;

R—O—O—H (wherein, R represents a monovalent hydrocarbon group), and is reacted with an olefin type compound to produce an olefin oxide compound and compound, R—OH. Preferably, the group R is a group having 3 to 20 carbon atoms. Most preferably, this is a hydrocarbon group having 3 to 10 carbon atoms, particularly a secondary or tertiary alkyl group or aralkyl group. Among them, tertiary alkyl groups and secondary or tertiary aralkyl groups are particularly preferable, and specific examples thereof include a tertiary butyl group, tertiary pentyl group, cyclopentyl group, and 2-phenylpropyl-2 group. Further, various tetralinyl groups formed by eliminating a hydrogen atom from an aliphatic side chain of a tetralin molecule, are also listed.

When cumene hydroperoxide as the organic hydroperoxide is used, the resulting hydroxyl compound is 2-phenyl-2-propanol. This can be converted into α-methyl styrene by dehydration reaction. α-methyl styrene is a industrially useful substance.

Tertiary amylene formed by dehydration of tertiary pentyl alcohol obtained by using tertiary pentyl hydroperoxide as the organic hydroperoxide, is a useful substance as a precursor of isoprene. Tertiary pentyl alcohol is useful as a precursor of methyl tertiary pentyl ether which is an octane booster.

Tertiary butyl alcohol obtained by using t-butyl hydroperoxide as an organic hydroperoxide is useful as a precursor of methyl tertiary butyl ether which is an octane booster.

Hydrogen peroxide can be listed as an example other than organic hydroperoxides.

Hydrogen peroxide is a compound represented by the chemical formula, HOOH, and can be obtained usually in the form of an aqueous solution. It reacts with an olefin type compound to form an oxirane compound and water.

The organic hydroperoxide and hydrogen peroxide, which are used as a raw material, may be a thin or dense purified or non-purified material.

The epoxidation can be carried out in a liquid phase by using a solvent and/or a diluent. The solvent and diluent are a substance which is liquid under the pressure and temperature under which the reaction is conducted, and must be substantially inert against the reactants and products. The solvent may be a substance existing in the hydroperoxide solution to be used. For example, when cumene hydroperoxide is a mixture of cumene hydroperoxide and cumene, which is a raw material thereof, said cumene hydroperoxide can be used as a substitute for the solvent without especially adding a solvent.

The epoxidation temperature is usually from 0 to 200° C., preferably from 25 to 200° C. The pressure may be a pressure enough to keep the reaction mixture liquid. Usually, the pressure is advantageously from 100 to 10000 kPa.

After completion of the epoxidation, a liquid mixture containing a desired product can be easily separated from a catalyst composition. Next, the liquid mixture is purified by a suitable method. Purification includes fractional distillation, selective extraction, filtration, washing and the like. The solvent, catalyst, non-reacted olefin type compound and non-reacted hydroperoxide can be used again by recycling.

The reaction, in which the catalyst of the present invention is used, can be carried out in the form of a slurry or a fixed bed, and, in the case of a large scale of industrial operation, it is preferable to use a catalyst in the form of a fixed bed. The present process can be carried out by a batchwise method, semi-continuous method or continuous method. When a solution containing a reactant is introduced through a fixed bed, a liquid mixture obtained from a reaction zone does not contain catalyst at all or contains substantially no catalyst.

EXAMPLE

The present invention is illustrated by the following Examples below.

Example 1

Preparation of Catalyst Powder 125.0 g of a template solution composed of 16% by weight of hexadecyltrimethyl ammonium hydroxide, 64% by weight of methanol and 20% by weight of water (water in the solvent is 20/(64+20)=24% by weight) was stirred, a mixed solution of 1.85 g of tetra-isopropyl orthotitanate and 10.0 g of 2-propanol was added dropwise to this at 50° C. After stirring of 30 minutes, 30.5 g of tetramethyl orthosilicate and 6.8 g of methyltrimethoxysilane were added dropwise. Thereafter, stirring was continued at 50° C. for 3 hours. Thus obtained precipitate was filtered. The precipitate obtained was dried at 70° C. for 8 hours under vacuum.

Preparation of Molded Body

A mixture obtained by sufficiently mixing 30.0 g of the dried white solid and 4.5 g of water with sprayer was compression-molded with a tabletting machine.

The obtained solid was pulverized, then molded catalyst of 1.0 to 2.0 mm was obtained using sieves. Solid smaller than 1.0 mm was recycled to conduct compression molding again.

Extractive Removal of Template

Next, 11.5 g of the molded body obtained as described above was packed in a glass column of an inside diameter of 16 mmφ, (1) 100 ml of methanol at room temperature, (2) a mixed liquid of 200 ml of methanol at 45° C. with 4.0 g of concentrated hydrochloric acid (content: 36% by weight) at 45° C., and (3) 200 ml of methanol at 45° C., in this order, were respectively passed through the column at LHSV of 6 h$^{-1}$ upwardly. After completion of passing through, methanol in the column was drawn from the bottom of the column. And, the molded catalyst was dried under vacuum of 10 mmHg and heating of at 80° C. for 1.5 hours.

Synthesis of Propylene Oxide (PO)

The molded catalyst obtained as described above was evaluated with a batch reaction apparatus (autoclave) using 25% of cumene hydroperoxide (CHPO) and propylene (C3'). 1.0 g of the catalyst, 30.0 g of CHPO and 16.6 g of C3' were charged in the autoclave to react them under autogenous pressure at a reaction temperature of 85° C. for a reaction time of 1.5 hours (containing temperature raising time). The reaction result is shown in Table 1.

Example 2

Silylation

The molded catalyst obtained in Example 1 of 3.0 g was charged in a glass flask jacketed with a cooling tube, and then, hexamethyldisilazane of 2.0 g and toluene of 30.0 g were added thereto to carry out the silylation under heating of 110° C. for 1.5 hours. After separation of the liquid, the molded catalyst was dried under heating of 110° C. and vacuum of 10 mmHg for 1.5 hours. The average pore diameter of thus obtained molded catalyst, the rate of the pore volume having a pore diameter of 5 to 200 Angstrom to the all pore volume and a specific pore volume measured by a physical adsorption method using nitrogen as a gas, were respectively 29 Angstrom, 94% and 0.87 ml/g. The obtained silylated catalyst was evaluated in the same manner as in Example 1. The reaction result is shown in Table 1.

Comparative Example 1

A molded catalyst was prepared and it was evaluated with a batch reaction apparatus in the same manner as in Example 1 except that 125.0 g of a template solution composed of 16% by weight of hexadecyltrimethylammonium hydroxide, 11% by weight of methanol and 73% by weight of water (water in the solvent: 73/(11+73)=87% by weight) was used. The reaction result is shown in Table 1.

Comparative Example 2

The molded catalyst obtained in Comparative Example 1 was silylated and evaluated in the same manner as in Example 2.
The reaction result is shown in Table 1.

Example 3

Preparation of Catalyst Powder 125.0 g of a template solution composed of 16% by weight of hexadecyltrimethylammonium hydroxide, 66% by weight of methanol and 18% by weight of water (water in the solvent is 18/(66+18)=21% by weight) was stirred, a mixed solution of 1.85 g of tetra-isopropyl orthotitanate and 10.0 g of 2-propanol was added dropwise to this at 50° C. After stirring of 30 minutes, a mixed solution of 15.2 g (100 mmol) of tetramethyl orthosilicate and 3.4 g (25 mmol) of methyltrimethoxysilane was added dropwise (first half). After adding 19.1 g (125 mmol) thereto (latter half), stirring was continued at 50° C. for 3 hours. Thus obtained precipitate was filtered. The precipitate obtained was dried at 70° C. for 8 hours under vacuum.

Preparation of Molded Body

A mixture which was obtained by sufficiently mixing 25.0 g of the dried white solid and 3.8 g of water with sprayer was compression-molded with a tabletting machine. The obtained solid was pulverized, then molded catalyst of 1.0 to 2.0 mm was obtained using sieves. Solid smaller than 1.0 mm was recycled to conduct compression molding again.

Extractive Removal of Template

Next, 11.5 g of the molded body obtained as described above was packed in a glass column of an inside diameter of 16 mmϕ, (1) 100 ml of methanol at room temperature, (2) a mixed liquid of 200 ml of methanol at 45° C. with 4.0 g of concentrated hydrochloric acid (content: 36% by weight) at 45° C., and (3) 200 ml of methanol at 45° C., in this order, were respectively passed through the column at LHSV of 6 $h^{-1}$ upwardly. After completion of passing through, methanol in the column was drawn from the bottom of the column. And, the molded catalyst was dried under vacuum of 10 mmHg and heating of at 80° C. for 1.5 hours.

Synthesis of Propylene Oxide (PO)

PO was synthesized in the same manner as in Example 1 except that the molded catalyst obtained as described above was used. The reaction result is shown in Table 1.

Example 4

A molded catalyst was prepared and evaluated with a batch reaction apparatus in the same manner as in Example 3 except that, in an addition of a silica source, after 19.1 g (125 mmol) of tetramethylorthosilicate was added dropwise in the first half, 15.2 g (100 mmol) of tetramethylorthosilicate and 3.4 g (25 mmol) of methyltrimethoxysilane were added dropwise in the latter half. The reaction result is shown in Table 1.

Example 5

A molded catalyst was prepared and evaluated with a batch reaction apparatus in the same manner as in Example 3 except that, in an addition of a silica source, a mixed solution of 30.4 g (200 mmol) of tetramethylorthosilicate and 6.8 g (50 mmol) of methyltrimethoxysilane was added dropwise in the first half and latter half, respectively. The reaction result is shown in Table 1.

TABLE 1

| | | Example 1 | Example 2 | Comparative Example 1 | Comparative Example 1 | Example 3 | Example 4 | Example 5 |
|---|---|---|---|---|---|---|---|---|
| Step A | Rate of water in solvent | 24 | 24 | 87 | 87 | 21 | 21 | 21 |
| (I) | Silylation | Absent | Present | Absent | Present | Absent | Absent | Absent |
| Step A (II) | Amount of organic silica source added in first half (mol) | 25 | 25 | 25 | 25 | 25 | 0 | 25 |
| | Amount of organic silica source added in latter half (mol) | 25 | 25 | 25 | 25 | 0 | 25 | 25 |
| | Total amount of organic silica source | 50 | 50 | 50 | 50 | 25 | 25 | 50 |

TABLE 1-continued

| | Example 1 | Example 2 | Comparative Example 1 | Comparative Example 1 | Example 3 | Example 4 | Example 5 |
|---|---|---|---|---|---|---|---|
| Reaction result | | | | | | | |
| CHPO Conversion % | 80.1 | 90.3 | 77.4 | 80.9 | 84.0 | 79.8 | 80.2 |
| PO/C3' Selectivity % *1 | 96.7 | 99.1 | 95.3 | 99.1 | 97.0 | 96.3 | 97.2 |

*1 PO/C3' Selectivity = Produced PO mol/Reacted C3' mol × 100

INDUSTRIAL APPLICABILITY

According to the present invention, there can be provided a process for producing a titanium-containing silicone oxide catalyst which can be used for a reaction obtaining, for example, an olefin oxide compound from a hydroperoxide and an olefin type compound and which can exhibit high activity and high selectivity, and a catalyst obtainable by the process.

The invention claimed is:

1. A process for producing a titanium-containing silicon oxide catalyst satisfying all of the following conditions (1) to (3), which comprises the following A and B steps:
   (1) an average pore diameter of 10 Å or more,
   (2) a pore diameter of 90% or more of the total pore volume of 5 to 200 Å, and
   (3) a specific pore volume of 0.2 cm³/g or more: and
   step A:
   (I) a step of obtaining a solid containing a catalyst component and a template by using a silicon compound in which a part or all of a hydrocarbon group is directly bonded to a silicon atom, as a silica source, and mixing the silica source with a titanium source and a solution of the template by stirring, wherein the rate of water in a solvent in the solution is 5 to 40% by weight, or
   (II) a step of obtaining a solid containing a catalyst component and a template by using an organic silica source composed of a silicon compound in which a hydrocarbon group is directly bonded to a silicon atom and an inorganic silicon source composed of a silicon compound not having a carbon-silicon bonding, as a silica source, and mixing the silica source with a titanium source and a solution of the template by stirring, wherein the following expression is satisfied in the addition of the silica source to the solution of the template, Amount of the organic silicon compound added in the first half>Amount of the organic silicon compound added in the latter half, wherein the first half means a period taken from the initiation of the addition to completion of the addition of the half mole of the amount of the total silica source; and
   Step B: a step of removing the template from the solid obtained in the step A.

2. The process according to claim 1, wherein the rate of water contained in the solvent of the solution of the template in the step A (II) is 50% by weight or lower.

3. The process according to claim 1, wherein the template used in the step A is a quaternary ammonium ion represented by the general formula (a), $$[NR^1R^2R^3R^4]^+ \qquad (a),$$

wherein, $R^1$ represents a linear or branched hydrocarbon group having 2 to 36 carbon atoms, and $R^2$ to $R^4$ represent an alkyl group having 1 to 6 carbon atoms.

4. The process according to claim 1, wherein the silicon compound in which the hydrocarbon group is directly bonded to a silicon atom used in the step A, is a monoalkyltrialkoxysilane and/or monoaryltorialkoxysilane.

5. The process according to claim 1, wherein the removal of the template in the step B is carried out by a solvent extraction.

6. The process according to claim 1, wherein the solid after removing the template is subjected to silylation.

7. A titanium-containing silicon oxide catalyst obtainable by the process according to claim 1.

8. A process for producing an olefin oxide compound, which comprises reacting an olefin type compound with a hydroperoxide in the presence of the catalyst of claim 7.

* * * * *